United States Patent [19]

Naik et al.

[11] Patent Number: 4,737,520

[45] Date of Patent: Apr. 12, 1988

[54] WATER-SOLUBLE PESTICIDAL FORMULATIONS

[75] Inventors: Arundev H. Naik; Hans U. Sieveking, both of Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 671,661

[22] Filed: Nov. 15, 1984

[30] Foreign Application Priority Data

Nov. 29, 1983 [DE] Fed. Rep. of Germany ....... 3343092

[51] Int. Cl.⁴ .................. A61K 31/275; A61K 31/215
[52] U.S. Cl. ...................................... 514/520; 514/531
[58] Field of Search ................ 424/304, 305; 514/520, 514/531

[56] References Cited

U.S. PATENT DOCUMENTS

| | | | |
|---|---|---|---|
| 4,107,302 | 8/1978 | Watanabe | 424/358 |
| 4,183,942 | 1/1980 | Engel | 424/304 |
| 4,183,950 | 1/1980 | Neumann et al. | 424/306 |
| 4,214,004 | 7/1980 | Plummer | 424/305 |
| 4,218,469 | 8/1980 | Fuchs et al. | 424/306 |
| 4,279,923 | 7/1981 | Fuchs et al. | 424/304 |
| 4,316,914 | 2/1982 | Coffee et al. | 424/305 |
| 4,325,969 | 4/1982 | Brown | 424/304 |
| 4,341,760 | 7/1982 | Matthewson | 424/304 |
| 4,344,960 | 8/1982 | Fuchs et al. | 424/305 |
| 4,443,438 | 4/1984 | Kasamatsu et al. | 424/304 |
| 4,474,815 | 10/1984 | Holan et al. | 424/327 |
| 4,479,968 | 10/1984 | Hyman et al. | 424/330 |
| 4,500,348 | 2/1985 | Hausmann et al. | 514/518 |

FOREIGN PATENT DOCUMENTS

| | | |
|---|---|---|
| 0055401 | 7/1982 | European Pat. Off. . |
| 0062181 | 10/1982 | European Pat. Off. . |
| 2187226 | 1/1974 | France . |

*Primary Examiner*—Sam Rosen
*Attorney, Agent, or Firm*—Sprung Horn Kramer & Woods

[57] ABSTRACT

A water-soluble pesticidal formulation approximately comprising in grams per liter 10 to 500 of at least one pyrethroid, 10 to 200 of a non-polar solvent having a solubility in water at 20° C. of 0.01 to 15 g/liter, 20 to 500 of at least one non-ionic emulsifier, 5 to 250 of at least one anionic emulsifier, up to 300 of a solvent having a solubility in water at 20° C. of at least 30 g/liter, up to 5 of a dyestuff, up to 50 of auxiliaries and up to 900 of water. The formulation will dissolve in water to give clear solutions.

14 Claims, No Drawings

WATER-SOLUBLE PESTICIDAL FORMULATIONS

The invention relates to water-soluble pesticidal formulations which not only are themselves clear and stable solutions but also give clear and stable solutions after dilution with water. The invention also relates to the preparation and use of these formulations.

Most organic pesticides are insoluble in water. They are therefore dissolved in organic solvents and are formulated as emulsifiable concentrates by the addition of emulsifiers. On dilution with water, a white emulsion is formed. If the pesticides were liquid, the solvent could be dispensed with, as described, for example, in U.S. Pat. No. 4,195,083. However, the emulsion formed with water is usually a white emulsion of coarse particle size.

A new direction in formulation technology in the last few years is particularly remarkable. The trend is to replace organic solvents with water, in particular to save costs, to reduce the toxicity and phytotoxicity, to offer products which do not pollute the environment and to ensure generally a higher safety for transporters and users.

DE-OS (German Published Specification) No. 3,011,611 relates to highly viscous (400 cp) suspensions containing thickeners. Such auxiliaries can only prevent sedimentation of the active compound in the concentrates but not in the dilutions in water, for example in cattle dips.

Thickeners are likewise used in DE-OS (German Published Specification) No. 2,924,878. The products are prepared at 70° C. with a high-speed (5,000 revolutions/minute) mixer.

The aqueous concentrates of European Patent Application No. 0,074,329 can be diluted with water, and relatively stable emulsions or dispersions thereby form.

European Patent Application No. 0,062,181 describes emulsions which, with particle sizes of 50 nm to 100 nm, do not give clear solutions.

Furthermore, clear systems which have been obtained using individual non-ionic emulsifiers have been described.

It has now been found, surprisingly, that it is not necessary to replace all of the non-polar solvent. In contrast, a small amount of such a solvent has proved to be very advantageous. When an anionic emulsifier is used in addition to the non-ionic emulsifier, it is possible to reduce the emulsifier requirement, especially for the pyrethroid pesticides. This allows formulations with higher active compound concentrations to be prepared. In the concentrations according to the invention, the content of non-polar solvents is usually below that of the active compound.

The invention accordingly relates to a water-soluble pesticidal formulation comprising of 10 to 500 g/liter of at least one pyrethroid, 10 to 200 g/liter of a solvent, the solubility of which in water at 20° C. is 0.01 to 15 g/liter, 20 to 500 g/liter of at least one non-ionic emulsifier, 5 to 250 g/liter of at least one anionic emulsifier, 0 to 300 g/liter of a solvent, the solubility of which in water is 30 to ∞ g/liter, 0 to 5 g/liter of a dyestuff, 0 to 50 g/liter of auxiliaries and 0 to 900 g/liter of water.

The concentrates according to the invention are miscible with water in all proportions, clear solutions being obtained, the homogeneity and stability of which are superior to the corresponding dilutions of other pesticide concentrates. This property is therefore of great importance where the application liquor is used over a long period, as is the case in spraying from a tractor, airplane or helicopter in the agricultural sector, in combating insects in the hygiene sector and in spraying and, in particular, dipping animals in the veterinary sector.

Non-polar solvents, the solubility of which in water is 0.01 to 2 g/liter at 20° C. are preferred. The solubility of the solvent which may additionally be used is preferably 50 to 300 g/liter at 20° C., but in particular 80 to 120 g/liter at 20° C.

Because of the use of surface-active agents and hydrophobic active compounds, the clear solutions are usually considered to be emulsions and are described as microemulsions.

The clear, stable solutions are a solubilized system, and in particular a "solubilized solution". According to Swarbrick (J. Pharm. Sci. 54 (1965) 1229–1237) and Shinoda/Kunieda (J. Colloid and Interface Sci. 42 (1973) 381–387) the thermodynamically stable micellar solutions should not be designated as microemulsions. According to these authors, such solutions are possible up to a micellesize of 100 nm. In the use dilutions of the formulations made according to this invention the particle size did not exceed 40 nm.

The concentrates according to the invention and their stable dilutions in water (spraywashes, dipwashes and the like) are quite easy to prepare. The active compound and the non-polar solvent are first mixed together with the emulsifiers to give a clear solution. If liquid emulsifiers are used, the mixing process can be carried out easily at room temperature.

After addition of the required amount of water, the components are mixed with a normal blade stirrer until a clear solution is formed. On addition of water, a gelatinous mass is first formed when the ratio of water to "non-polar solvent/emulsifier" has reached about 1:1. The last mixing stage is made easier by using warm (30° C.–40° C.) water, but also by using a small amount of polar solvent, which inhibits gel formation. The preparation process is then simplified such that the product can be prepared directly, for example in a bottle, without the additional use of any apparatus. The spontaneous formation of the formulation with only a low energy consumption demonstrates that the system is stable.

There is also a further advantage in using the non-polar organic solvent, because the stock of active compound can be kept as a presolution in this solvent. In the preparation of the formulation according to the invention, it is then no longer necessary to melt the active compound each time, if it is semi-solid to solid, since it is already available in a free-flowing form as a presolution.

Examples of pyrethroids which can be used according to the invention are: (α-cyano-4-fluoro-3-phenoxy)-benzyl 3-[2-(4-chlorophenyl)-2-chlorovinyl]-2,2-dimethylcyclopropanecarboxylate (flumethrin), α-cyano-3-phenoxybenzyl (+)-cis, trans-3-(2,2-dibromovinyl)-2,2-dimethylcyclopropanecarboxylate (deltamethrin), α-cyano-3-phenoxybenzyl 2,2-dimethyl-3-(2,2-dichlorovinyl)-cyclopropanecarboxylate (cypermethrin), 3-phenoxybenzyl (+)-cis, trans-3-(2,2-dichlorovinyl)-2,2-dimethylcyclopropanecarboxylate (permethrin, α-cyano-3-phenoxybenzyl α-(p-Cl-phenyl)-isovalerate (sumizidin), cyano-(3-phenoxyphenyl)-methyl 3,3-spiro-[cyclopropane-1,1-(1H)-indene]-2-carboxylate (cypothrin), 5-benzyl-3-furyl-methyl (+)-cis, trans-chrysanthemates (resmethrin);

2-methyl-4-oxo-3-(penta-2,4-dien-1-yl)-cyclopent-2-en-1-yl, 2,2-dimethyl-3-(2-X-2-methyl-1-propenyl)-cyclopropane-carboxylate (Pyrethrin I X=—CH₃; Pyrethrin II X=—CO—O—CH₃); α-cyano-(4-fluoro-3-phenoxyphenyl)-methyl-3-(2,2-dichloro-vinyl)-2,2-dimethylcyclopropanecarboxylate (cyfluthrin) and pentafluorophenyl-methyl-3-(2,2-dichloroethenyl)-2,2-dimethylcyclopropanecarboxylate (fenfluthrin)

The following organic, non-polar solvents are preferred according to the invention: Solvesso 200 (Esso Chemie GmbH): high-boiling (219°-282° C., DIN 51 751) solvent consisting chiefly (98%) of C₁₀-C₁₃-aromatics; Solvesso 150 (Esso Chemie GmbH): boiling range 186°-205° C., aromatic content 99%; Shellsol A (Shellchemie): boiling range 165°-199° C.; Shellsol AB (Shellchemie): boiling range 186°-210° C.; Shellsol RA (Shellchemie): boiling range 178°-325° C.; Aromasol H (Imperial Chemical Industries); 1-octanol; and diisobutyl ketone.

Preferred non-ionic emulsifiers which can be used are alkylaryl polyglycol ethers of the formula

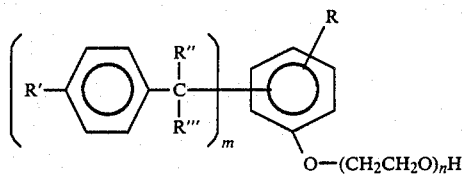

wherein
R is H or phenyl,
R' is H or alkyl with 1 to 20 carbon atoms,
R" and R''' each independently is H, methyl or ethyl
m is from 1 to 3 (including, for example, 1.35), and
n is an integer from 8 to 50.

The following may be mentioned as examples of the non-ionic emulsifiers: Emulgator OX (Bayer AG): alkyl polyglycol ether; Emulgator 1736 (Bayer AG): alkyl polyglycol ether; Emulgator 1371 B (Bayer AG): alkyl polyglycol ether; Emulsogen EL (Hoechst AG): oxyethylated fatty acid derivative; Emulgator 368 (Bayer AG): alkylaryl polyglycol ether; Emulgator 373 (Bayer AG): alkylaryl polyglycol ether; Emulgator SZZ 1147 A (Bayer AG): alkylaryl polyglycol ether; Emulgator SZZ 14 (Bayer AG): alkylaryl polyglycol ether; Emulgator SZZ 1166 B (Bayer AG): alkylaryl polyglycol ether; Emulgator W (Bayer AG): alkylaryl polyglycol ether; Arlatone 650 (Atlas): polyoxyethylene castor oil ester; Triton x-100 (Rohm-Haas): isooctylphenol-polyethoxyethanol; and Ninox BM 2 (Stepan): ethoxylated nonylphenol.

Preferred anoinic emulsifiers are salts of inorganic or organic bases and sulphonic acids of the formula R—C₆H₄—SO₃H wherein R is an alkyl radical with 5 to 30 carbon atoms.

The following are examples of anionic emulsifiers: Emulgator 1371 A (Bayer AG): calcium n-dodecylbenzenesulphonate, 67% strength in n-butanol; Phenylsulfonat CA (Hoechst): calcium alkylarylsulphonate, 70% in isobutanol; Emulgator 110 f (Bayer AG): n-dodecylbenzene sulphonic acid monoethanolamine salt; Emulgator SZZ 1328 (Bayer AG): n-dodecylbenzene sulphonic acid sodium salt; and Emulgator SZZ 1328 C (Bayer AG): n-dodecylbenzene sulphonic acid ammonium salt.

The following can be used as polar solvents, the solubility of which in water is 30 to ∞ g/liter at 20° C.: isopropanol, n-butanol, triethylene glycol, dipropylene glycol, tripropylene glycol, polyethylene glycol 200, diethyleneglycol monoethyl ether (carbitol, ethyldiglycol), dipropylene glycol monomethyl ether and triethylene glycol monomethyl ether.

The types of dyestuff which can be used according to the invention are illustrated by the following example: acriflavine, azorubin S, indigotin, crystal violet, methyl violet, patent blue, rivanol, tartrazine and the like.

PREPARATION EXAMPLES

Example 1

25 g of Solvesso were taken. 60 g of the active compound flumethrin, liquefied at 70° C., were added and the components were mixed together at 60° C.-70° C. using a normal magnetic stirrer. 60 g of diethylene glycol monoethyl ether, 144 g of Emulgator SZZ 14 and 42 g of Emulgator 1371 A were then added stepwise at room temperature, with stirring. After a clear solution had formed, water was added, under the same stirring operation, until the volume was 1,000 ml. A clear yellow-brown solution was formed almost spontaneously.

After being stored for four months, this concentrate proved to be physically and chemically stable:

| Period | Appearance | Active compound content |
|---|---|---|
| Initially | clear yellow-brown solution | 58.6 g/liter |
| After 4 months | | |
| at 30° C. | unchanged | 58.8 g/liter |
| at 40° C. | unchanged | 58.7 g/liter |

The 6% strength formulation was spontaneously dilutable with water in all proportions. When diluted several times with water, for example 1:2,000 (=active compound concentration of 30 ppm), a colorless, crystalclear solution which could not be differentiated from water was formed.

This 1:2,000 dilution contained an average micelle size of 5 nm, measured by means of laser scattered light correlation spectroscopy.

The concentrate, with a viscosity of 21 mPs, was easily pourable. The flashpoint was above 100° C.

Example 2

A formulation was prepared as in Example 1, but with Emulgator 368 instead of Emulgator SZZ 14.
The viscosity was 27 mPs.
In vitro testing of this formulation against OP-resistant Biarra strains of Boophilus microplus showed a very good activity. When the formulation was diluted stepwise up to 60,000 times in water, 100% activity was observed.

The particle size in a 1:1,500 dilution in water, corresponding to an active compound concentration of 40 ppm, had an average value of 12 nm, measured by the method of laser scattered light correlation spectroscopy.

Example 3

The amount of emulsifier in the formulation of Example 2 was reduced to ⅔. The new formulation containing 60 g/liter of flumethrin, 30 g/liter of Solvesso 200, 90 g/liter of Emulgator 368, 30 g/liter of Emulgator 1371 A and the remainder as water was stilll clear after 8 months.

An active compound: emulsifier ratio of 1:2 has thus become possible. Without the addition of anionic emulsifier and non-polar solvent, the ratio is 1:5 or more.

The invention described here saves costs and permits higher concentrations of active compound.

Example 4

A 3% strength formulation and a 2% strength formulation were prepared from the 6% strength formulation of Example 3 by adding water. After 8 months, the clarity of the two new formulations was unchanged.

The preparation of formulations with lower concentrations of active compound has thereby been simplified.

Example 5

An 18% strength w/w formulation was prepared using 180 g/kg of flumethrin, 70 g/kg of Solvesso 200, 432 g/kg of Emulgator 368, 126 g/kg of Emulgator 1371 A, 126 g/kg of diethylene glycol monoethyl ether and water as the remainder.

The use concentrations can be prepared by direct dilution of this formulation with water. For practical dilution rates, however, formulations with lower active compound concentrations, like those of Examples 1 to 4, can also be prepared simply by addition of water. The particle size of a 1:1,000 dilution in water was 7 nm.

Example 6

A formulation of 150 g/liter of flumethrin, 90 g/liter of Solvesso 200, 100 g/liter of Emulgator 368, 50 g/liter of Emulgator 1371 A and water as the remainder gave, after 1:3,000 dilution in water, corresponding to an active compound concentration of 50 ppm and an emulsifier concentration of 50 ppm, an average particle size of 22 nm, by the method of laser scattered light correlation spectroscopy. This result was achieved by an even more advantageous active compound:emulsifier ratio of 1:1.

Because the polar solvent has been omitted, this formulation needs stirring for a longer time, but this can be shortened by heating to about 40° C.

Example 7

A formulation of the following composition was prepared: 50 g/liter of flumethrin active compound, 10 g/liter of fenfluthrin active compound, 14 g/liter of Solvesso 200, 2.8 g/liter of Aromasol H, 200 g/liter of n-butanol, 160 g/liter of Emulgator 368, 40 g/liter of Emulgator 1371 A and water as the remainder.

The particle size in a dilution of 1:500 was 18 nm.

Example 8

The 50+10 g/liter formulation of Example 7 is diluted, for example 1:1,000 with water, for spraying, for example, animals, an active compound concentration of 50+10 ppm being achieved in the spray liquor. In contrast, a higher active compound concentration, for example of 2,500+500 ppm=2.5+0.5 g/liter, is required for pour-on applications.

Such ready-to-use pour-on formulations can be prepared from the formulations according to the invention, and in particular quite simply by mixing together the components according to the following example:
50+10 g/liter of formulation according to Example 7

50 ml

| -continued | |
|---|---|
| 1-Octanol | 80 g |
| Isopropanol | 340 g |
| Water | to 1,000 ml |

This formulation has a low surface tension of 27 mN/m (dyn/cm), which means that good wetting, for example of the coat of hair of the animals, is effected.

It is possible to prepare other ready-to-use formulations, for example aerosol sprays, by the same principle.

The formulations according to the invention can thus also be used as concentrates for the preparation of ready-to-use products.

Example 9

This example describes a combination formulation.

| Flumethrin active compound | 30 g |
|---|---|
| Cyfluthrin active compound | 30 g |
| Aromasol H | 8.3 g |
| Solvesso 200 | 8.3 g |
| n-Butanol | 100 g |
| Emulgator SZZ 14 | 150 g |
| Emulgator 1371 A | 40 g |
| Water | to 1,000 ml |

A particle size of 5 nm was measured in a 1:600 dilution in water.

Example 10

A 30% strength w/w or w/v formulation can be prepared according to the following composition:

| Flumethrin active compound | 300 g |
|---|---|
| Solvesso 200 | 130 g |
| Emulgator 368 | 347 g |
| Emulgator 1371 A | 153 g |
| Water | to 1,000 g or 1,000 ml |

A 1:1,000 dilution in water gave a particle size of 17 nm and a 1:3,000 dilution gave a particle size of 16 nm.

It will be understood that the specification and examples are illustrative but not limitative of the present invention and that other embodiments within the spirit and scope of the invention will suggest themselves to those skilled in the art.

What is claimed:

1. A water-soluble pesticidal formulation approximately comprising in grams per liter 10 to 500 of one or more pyrethroids, 10 to 200 of an aromatic petroleum fraction boiling above about 165° C. having a solubility in water at 20° C. of 0.01 to 15 g/liter, 20 to 500 of one or more non-ionic emulsifiers, 5 to 250 g/liter of one or more anionic emulsifiers, 0 to 300 g/liter of a solvent having a solubility in water at 20° C. of at least 30 g/liter, 0 to 5 g/liter of a dyestuff, 0 to 50 g/liter of auxiliaries and 0 to 900 g/liter of water and which formulation is itself a clear and stable solution and is a clear and stable solution after dilution with water.

2. A water-soluble pesticidal formulation according to claim 1, containing (α-cyano-4-fluoro-3-phenoxy)-benzyl 3-[2-(4-chlorophenyl)-2-chlorovinyl]-2,2-dimethylcyclopropanecarboxylate as the pyrethroid.

3. A water-soluble pesticidal formulation according to claim 1, containing pentafluorophenyl-methyl 3-(2,2-dichloroethenyl)-2,2-dimethylcyclopropanecarboxylate as the pyrethroid.

4. A water-soluble pesticidal formulation according to claim 1, containing cyano-(4-fluoro-3-phenoxyphenyl)-methyl 3-(2,2-dichloroethenyl)-2,2-dimethylcyclopropanecarboxylate as the pyrethroid.

5. A water-soluble pesticidal formulation according to claim 1, wherein the particle size of the formulation after dilution with water is below 40 nm.

6. A water-soluble pesticidal formulation according to claim 1, wherein the solvent having a solubility in water at 20° C. of at least 30 g/liter is n-butanol.

7. A water-soluble pesticidal formulation according to claim 1, wherein the solvent having a solubility in water at 20° C. of at least 30 g/liter is diethylene glycol monoethyl ether, dipropylene glycol monomethyl ether or polyethylene glycol with an average molecular weight of 200.

8. A water-soluble pesticidal formulation according to claim 1, wherein the non-ionic emulsifier is an alkylaryl polyglycol ether of the formula

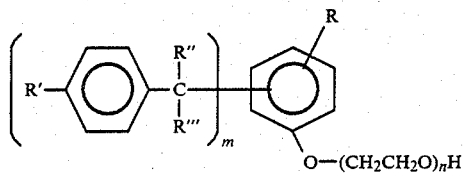

R—@/herein acid
R is H or phenyl,
R' is H or alkyl with 1 to 20 carbon atoms,
R" and R'" each independently is H, methyl or ethyl,
m is from 1 to 3, and
n is an integer from 8 to 50.

9. A water-soluble pesticidal formulation according to claim 1, wherein the anionic emulsifier is a salt of an inorganic or organic base and a sulphonic acid of the formula $R—C_6H_4—SO_3H$ wherein
R is an alkyl radical with 5 to 30 carbon atoms.

10. A process for the preparation of a water-soluble pesticidal formulation containing about 10 to 500 g/liter of a pyrethroid of claim 1, comprising dissolving the pyrethroid in the aromatic petroleum fraction and mixing the solution with one or more non-ionic emulsifiers and one or more anionic emulsifiers to give a clear and stable solution and a clear and stable solution after dilution with water.

11. A process according to claim 10, wherein the pyrethroid is first dissolved in a solvent having a solubility in water at 20° C. of at least 30 g/liter, and this presolution is mixed, as required, with the other components to give a clear solution.

12. A process according to claim 10, including mixing the solution with a solvent having a solubility in water of at least 30 g/liter at 20° C.

13. In the application of a pyrethroid to a field, crop or animal including the steps of making a pyrethroid-containing aqueous formulation, and then applying the formulation to said field, crop or animal in a pesticidally effective amount, the improvement which comprises making the formulation by adding water to a water-soluble concentrated formulation according to claim 1.

14. A water-soluble formulation according to claim 1, wherein the anionic emulsifier is a salt of an inorganic or organic of base 6-$H_4—SO_3H$ wherein
R is an alkyl radical with 5 to 30 carbon atoms, the non-polar solvent is a high boiling mixture of $C_{10}$–$C_{13}$ aromatic compounds, and the solvent having a solubility in water at 20° C. of at least 30 g/liter is polyethylene glycol.

* * * * *

UNITED STATES PATENT AND TRADEMARK OFFICE
CERTIFICATE OF CORRECTION

PATENT NO. : 4,737,520
DATED : Apr. 12, 1988
INVENTOR(S) : Naik et al.

It is certified that error appears in the above-identified patent and that said Letters Patent is hereby corrected as shown below:

| | |
|---|---|
| Title Page, under "U.S. Patent Documents", line 3 | Correct spelling of --Naumann-- |
| Col. 2, line 58 | Delete "(+)" and substitute --($\pm$)-- |
| Col. 2, line 62 | Delete "(+)" and substitute --($\pm$)-- |
| Col. 2, line 68 | Delete "(+)" and substitute --($\pm$)-- |
| Col. 8, line 29 | Delete "of base 6-" and substitute --base and a sulphonic acid of formula $R-C_6$-- |

Signed and Sealed this

Seventh Day of February, 1989

Attest:

DONALD J. QUIGG

Attesting Officer     Commissioner of Patents and Trademarks